United States Patent
Kakizuka et al.

(10) Patent No.: US 6,905,815 B2
(45) Date of Patent: Jun. 14, 2005

(54) METHOD OF SCREENING FOR INHIBITORS OF VCP BINDING TO POLYGLUTAMINE, ABETA, ALPHA-SYNUCLEIN, AND SOD1

(75) Inventors: Akira Kakizuka, Osaka (JP); Miho Hirabayashi, Osaka (JP)

(73) Assignees: Japan Science and Technology Corporation, Saitama (JP); Osaka Bioscience Institute, Osaka (JP)

( * ) Notice: Subject to any disclaimer, the term of this patent is extended or adjusted under 35 U.S.C. 154(b) by 136 days.

(21) Appl. No.: 10/111,373
(22) PCT Filed: Aug. 24, 2001
(86) PCT No.: PCT/JP01/07278
§ 371 (c)(1),
(2), (4) Date: Jun. 27, 2002
(87) PCT Pub. No.: WO02/16938
PCT Pub. Date: Feb. 28, 2002

(65) Prior Publication Data
US 2003/0138855 A1 Jul. 24, 2003

(30) Foreign Application Priority Data
Aug. 24, 2000 (JP) .................................. 2000-254412

(51) Int. Cl.[7] ..................... G01N 33/00; G01N 33/53; G01N 33/566
(52) U.S. Cl. ..................... 435/4; 435/7.1; 435/7.2; 435/7.21; 436/501; 800/3
(58) Field of Search ..................... 435/4, 7.1, 7.2, 435/7.21, 5, 325; 436/501; 800/3

(56) References Cited

PUBLICATIONS

American Heritage Dictionary of the English Language (downloaded from Dictionary.com Jan. 24, 2005).*
American Heritage Dictionary of the English Language (2000).*

Tobin & Signer (Dec. 2000) "Huntington's disease: the challenge for cell biologists." Trends Cell Biol. 10(12): 531–536.*

Barrow et al. (Jun. 20, 1992) "Solution conformations and aggregational properties of synthetic amyloid beta–peptides of Alzheimer's disease. Analysis of circular dichroism spectra." J Mol Biol. 225(4): 1075–1093.*

Johnstone et al. (Jul. 1991) "Conservation of the sequence of the Alzheimer's disease amyloid peptide in dog, polar bear and five other mammals by cross–species polymerase chain reaction analysis." Brain Res Mol Brain Res. 10(4): 299–305.*

Sian et al. (1999) "Parkinson's disease: a major hypokinetic basal ganglia disorder." J Neural Transm. 106(5–6): 443–476.*

Egerton et al. (Oct. 1992) "VCP, the mammalian homolog of cdc48, is tyrosine phosphorylated in response to T cell antigen receptor activation." EMBO J. 11(10): 3533–3540.*

Dai & Li (Aug. 2001) "Valosin–containing protein is a multi–ubiquitin chain–targeting factor required in ubiquitin–proteasome degradation." Nat Cell Biol. 3(8): 740–744.*

(Continued)

Primary Examiner—Elizabeth Kemmerer
Assistant Examiner—Christopher James Nichols
(74) Attorney, Agent, or Firm—Wenderoth, Lind & Ponack, L.L.P.

(57) ABSTRACT

A method for screening substances which are useful as effective components of prophylactic or therapeutic drug for neurodegenerative diseases caused by the binding of an aberrant protein and a valosin-containing protein, wherein the aberrant protein and the valosin-containing protein and the candidate substance are made to coexist, and the substance that shows inhibitory action on the binding of the aberrant protein and the valosin-containing protein is identified, is provided.

7 Claims, 5 Drawing Sheets

OTHER PUBLICATIONS

Zhang et al. (May 2000) "VCP, a weak ATPase involved in multiple cellular events, interacts physically with BRCA1 in the nucleus of living cells." DNA Cell Biol. 19(5): 253–263.*

National Library of Medicine (MeSH) (Jun. 4, 2004).*

Kakizuka, Tanpakushitsu, Kakusan, Kouso, vol. 45, No. 6, pp. 792–797 (2000).

Kakizuka, Trend Genet., vol. 14, No. 10, pp. 396–402 (1998).

Rockel, FEBS Lett., 451(1), pp. 27–32 (1999).

* cited by examiner a b

METHOD OF SCREENING FOR INHIBITORS OF VCP BINDING TO POLYGLUTAMINE, ABETA, ALPHA-SYNUCLEIN, AND SOD1

TECHNICAL FIELD

The invention of the present application relates to a method for screening substances that are useful as the effective components in prophylactic or therapeutic drugs for neurodegenerative diseases and a screening kit that uses such method. More particularly, the invention relates to a method for screening substances that inhibit the binding of known aberrant proteins that cause neurodegenerative diseases to valosin-containing protein (VCP), thereby identifying substances that are useful as the effective components of prophylactic or therapeutic drugs for neurodegenerative diseases. The invention further relates to a screening kit that is based on such method.

BACKGROUND ART

Neurodegenerative diseases such as Parkinson's disease, Alzheimer's disease, Huntington's chorea, and Machado-Joseph disease, occurs at a rate of one person in 10 thousand to 30 thousand for each disease. In Japan alone, the existence of more than 100 thousand patients (one person per 1,200) has been confirmed (Ministry of Welfare; Journal of Health and Welfare Statistics, 1996). Therefore, much effort has been made on the research of preventative and therapeutic methods (Borlongan, C. V., Koutouzis, T. K., Sanberg, P. R., Neurosci. Biobehav. Rev. 21, 289–93 (1997); Parnetti, L., Senin, U., Mecocci, P., The way forward. Drugs. 53, 752–68 (1997); Pasinetti, G. M., Neurobiol. Aging. 17, 707–16 (1996)). Studies have found that neurodegenerative diseases share a common phenotype. That is, it has been confirmed that the aggregation and accumulation of aberrant proteins, which have distinctive characteristics such as extended glutamine chain, abnormal conformation, resistance to proteases, β-sheet structure, etc., cause the formation of vacuoles and cell death cells (Kakizuka, A., Trends Genet. 14, 396–402 (1998)).

However, the causal matter that is involved in the induction of aggregation and accumulation of such aberrant proteins, which then cause the formation of vacuoles and cell death, is yet to be identified, thereby delaying the research and development of remedies and prophylactics for neurodegenerative diseases.

The inventors of the present application have, through assiduous work, succeeded in identifying the factor that induces the phenotype common to such neurodegenerative diseases, and revealed that the factor is a valosin-containing protein (VCP)

VCP, an AAA (ATPase Associated with various cellular Activities) super family protein existing generally in organisms ranging from eucaryotic cells to humans, has a weak ATPase activity and has been considered to be involved in various cell functions, particularly signal transduction (Muller, J M., Meyer, H. H., Ruhrberg, C., Stamp, G. W., Warren, G., Shima, D. T., J. Biol. Chem. , 274, 10154–10162 (1999); Zhang, L., Ashendel, C. L., Becker, G. W., Morre, D. J., J. Cell Biol., 127, 1871–1883 (1994)). However, VCP was not known to be a factor that induces neurodegenerative diseases by binding with aberrant proteins.

On the basis of this new finding, it is expected that by establishing a method for screening substances that inhibiting the binding of VPC and the aberrant protein, substances that are commonly effective as therapeutic or prophylactic drugs for a specific disease, as well as for a series of neurodegenerative diseases may be obtained.

The invention of the present application was made in view of the above-described situation, and its object is to solve the problems of the prior art and to provide a method for screening substances useful as effective components in prophylactic or therapeutic drugs for neurodegenerative diseases.

DISCLOSURE OF INVENTION

In order to solve the above-described problems, the present invention firstly provides a method for screening substances which are useful as effective components of prophylactic or therapeutic drug for neurodegenerative diseases caused by the binding of an aberrant protein and a valosin-containing protein, comprising: making the aberrant protein and the valosin-containing protein and the candidate substance coexist; and identifying the substance that shows inhibitory action on the binding of the aberrant protein and the valosin-containing protein.

Secondly, the present invention provides the above method for screening substances, wherein the aberrant protein is a protein that contains an extended glutamine-chain; thirdly, the present invention provides the above method for screening substances, wherein the aberrant protein contains an abnormal conformation; fourthly, the present invention provides the above method for screening wherein the aberrant protein is a protease-resistant protein; and fifthly, the present invention provide the above method for screening a substance, wherein the aberrant protein contains a β-sheet structure.

Further, the present invention sixthly provides the above-described method of screening substances, wherein the aberrant protein and the valosin-containing protein and the candidate substance are made to coexist by mixing in a solution; the present invention seventhly provides the above method for screening a substance, wherein the aberrant protein and the valosin-containing protein and the candidate substance are made to coexist in a cultured cell; the present invention eighthly provides the method for screening a substance, wherein the aberrant protein and the valosin-containing protein and the candidate substance are made to coexist by administering each component to an animal.

Furthermore, ninthly, the present invention provides the above method for screening substances, wherein the inhibitory action is detected by immobilizing the non-labeled protein on a carrier; contacting the aberrant protein and the valosin-containing protein in the presence of the candidate substance; and detecting the signal generated by the labeled protein on the immobilized carrier.

Also, the present invention tenthly provides a kit for screening substances which are useful as effective components of prophylactic or therapeutic drug for neurodegenerative diseases caused by the binding of an aberrant protein and a valosin-containing protein, comprising:
a carrier on which the valosin-containing protein is immobilized; and a labeled aberrant protein reagent.

Finally, the present invention eleventhly provides a kit for screening substances which are useful as effective components of prophylactic or therapeutic drug for neurodegenerative diseases caused by the binding of an aberrant protein and a valosin-containing protein, comprising: a labeled valosin-containing protein reagent; and a carrier on which the aberrant protein is immobilized.

1: Intrinsic VCP protein in the PC12 cells (a) fluorescence micrograph; (b) optical micrograph.

2: Fluorescence micrograph 48 hours after the removal of tetracycline (a) The intrinsic VCP stained with an anti-VCP antibody (second antibody=FITC-labeled anti-rabbit antibody) in PC12/Q79; (b) Polyglutamine stained with anti-Flag antibody (second antibody=texas red-labeled anti-mouse antibody) and the DAPI-stained nucleus in PC12/Q79; (c) Superposition of the intrinsic VCP stained with an anti-VCP antibody (second antibody=FITC-labeled anti-rabbit antibody) and polyglutamine stained with an anti-Flag antibody (second antibody=texas red-labeled anti-mouse antibody) in PC12/Q79; (d) Optical micrograph of PC12/Q79.

3: Fluorescence micrograph 96 hours after the removal of tetracycline (a) The intrinsic VCP stained with an anti-VCP antibody (second antibody=FITC-labeled anti-rabbit antibody) in PC12/Q79; (b) Polyglutamine stained with anti-Flag antibody (second antibody=texas red-labeled anti-mouse antibody) and the DAPI-stained nucleus in PC12/Q79; (c) Superposition of the intrinsic VCP stained with an anti-VCP antibody (second antibody=FITC-labeled anti-rabbit antibody) and polyglutamine stained with an anti-Flag antibody (second antibody=texas red-labeled anti-mouse antibody) in PC12/Q79; (d) Optical micrograph of PC12/Q79.

Figure 2:
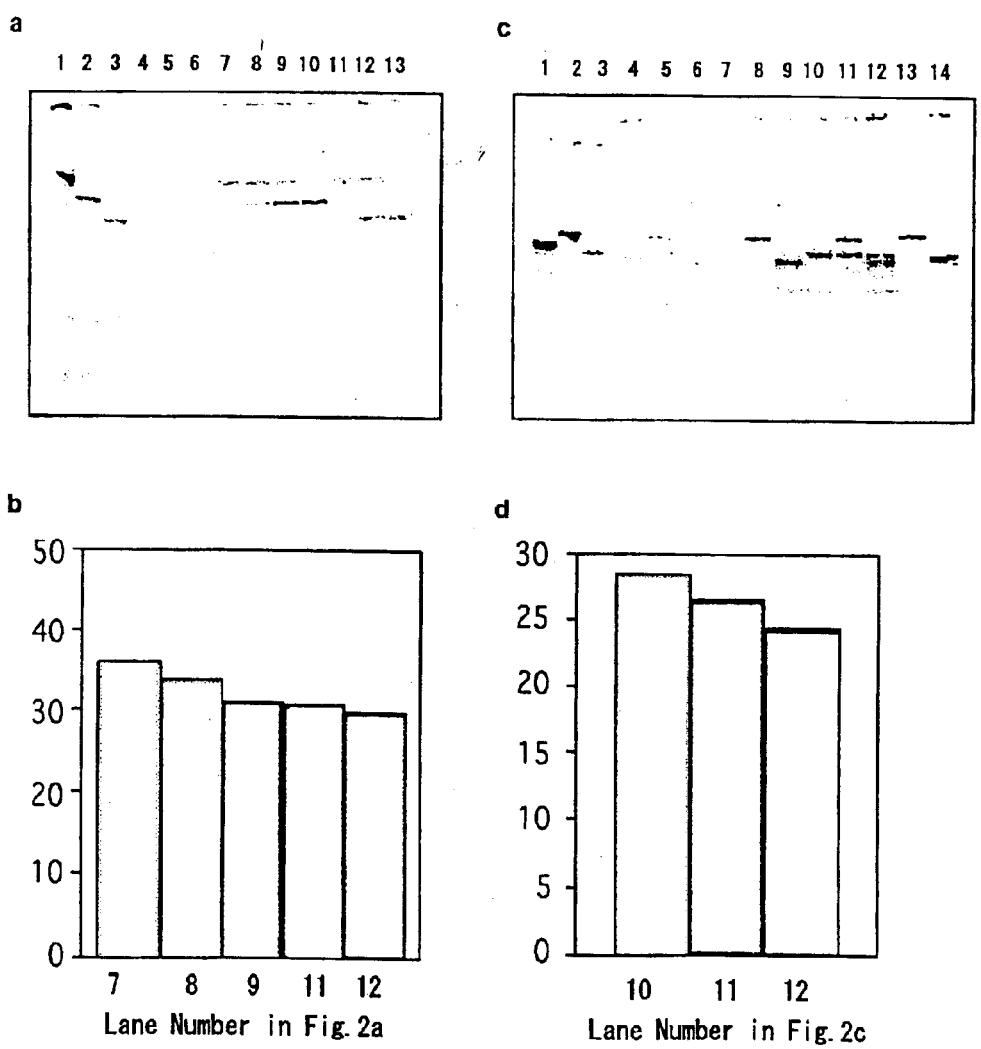

FIG. 2 shows the results of autoradiography for confirming whether the binding inhibition of MJDQ79 and VCP occurs when a chaperone protein (Hsp70, or HJD-2) coexists with VCP and GST-MJDQ7 in the Example of the present invention. (a) Interaction of GST-MJDQ79 and VCP when the amount of Hsp70 or HJD-2 coexisting with GST and GST-MJDQ79 was changed; with input of VCP, Hsp70 and HJD-2 expressed as 1 with reference to lanes 1 to 13. (b) A graph expressing lanes 7, 8, 9, 11 and 12 in FIG. 2a (interaction of VCP with GST-MJDQ79) numerically. (c) Interaction of GST-VCP with MJDQ79 when the amount of Hsp70 or HJD-2 coexisting with GST and GST-VCP was changed; with the input of MJDQ79, Hsp70 and HJD-2 expressed as 1 with reference to lanes 1 to 14. (d) A graph in expressing lanes 10, 11 and 12 in FIG. 2c (interaction of GST-VCP with MJDQ79) numerically.

Figure 3:
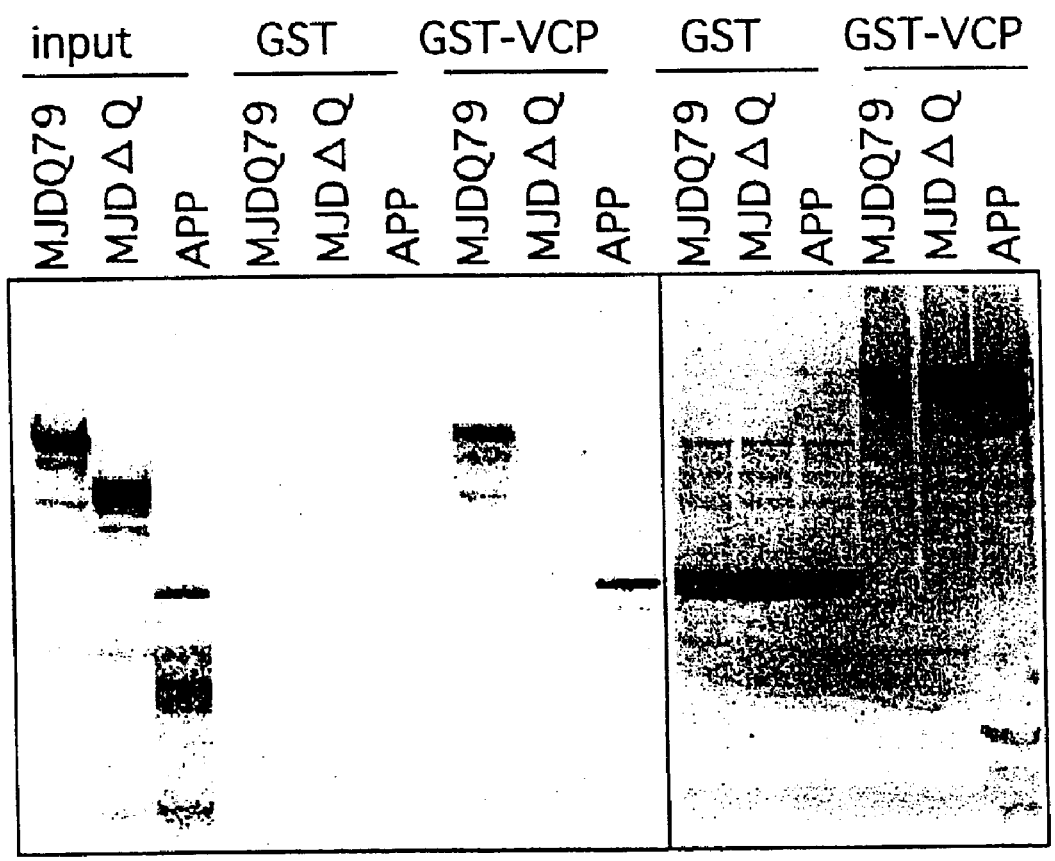

FIG. 3 shows the results of autoradiography indicating the binding of a precursor protein of amyloid β-protein and VCP in the Example of the present invention.

Figure 4:
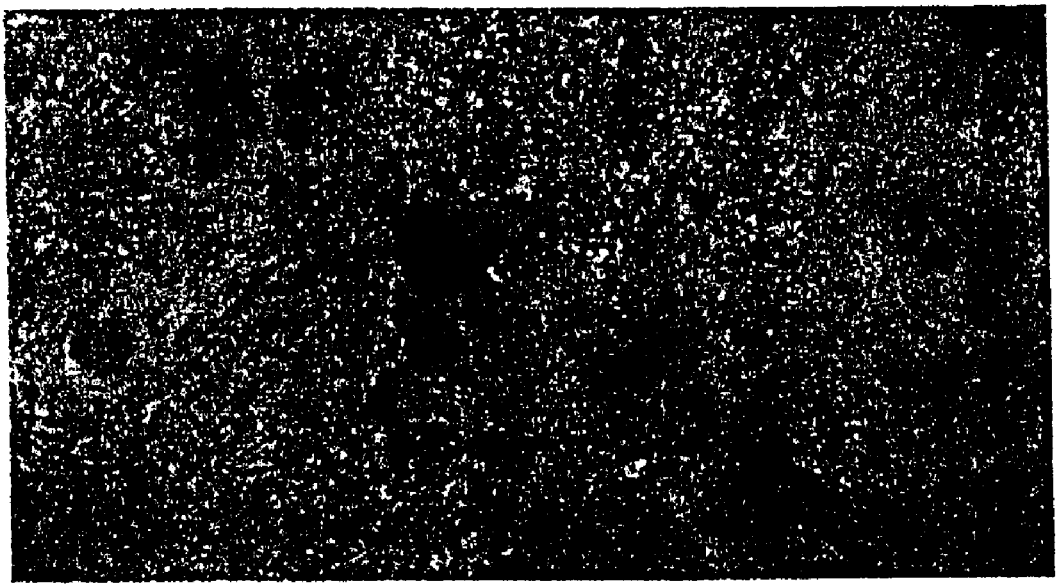

FIG. 4 shows a micrograph of the Lewy bodies in DLB stained with anti-VCP antibody in the Example of the present invention. (▼)

Figure 5:
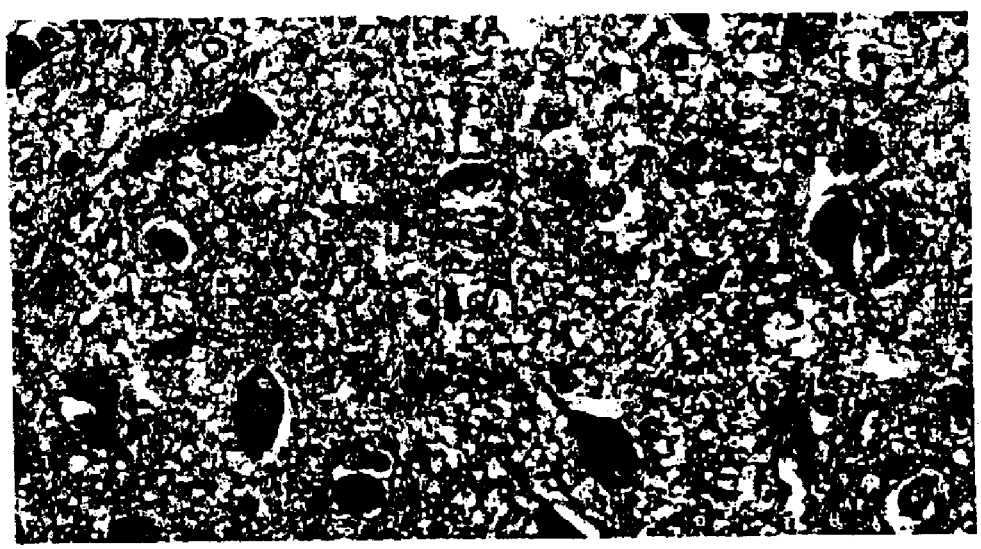
Figure 5:

FIG. 5 shows a micrograph of ubiquitin-positive nuclear inclusion bodies stained in the Example of the present invention. (a) Stained with anti-ubiquitin antibody; (b) Stained with anti-VCP antibody.

BEST MODE FOR CARRYING OUT THE INVENTION

The inventors of the present application have found, through assiduous work, that neurodegenerative diseases are induced by the binding of an aberrant protein to a valosin-containing protein (VCP), which causes degeneration and omission of nerve cells, and completed the method for screening substances useful as effective components in prophylactic or therapeutic drugs for neurodegenerative diseases of the present invention.

In the invention of the present application, the term aberrant protein means proteins which aggregate and accumulate in the nerve cells to cause vacuolization and cell death. For example, aberrant proteins include proteins that contain an extended glutamine chain, proteins that contain abnormal conformation, proteins that are protease-resistant and proteins with a β-sheet structure.

The method for screening substances of the present invention comprises making an arbitrary aberrant protein and a candidate substance and VCP coexist, and confirming whether the binding of the aberrant protein and the valosin-containing protein is inhibited or not, thereby screening the substance which would become the effective component in prophylactic or therapeutic drugs for neurodegenerative.

In this screening method, the method by which the aberrant protein, VCP and candidate substance are made to coexist is not particularly limited. For example, an aberrant protein and VCP may be mixed in a solution in the presence of a candidate substance, making them coexist in solution, or each component may be incubated in yeast or cultured cells (including bacteria) and made to coexist. In addition, VCP may be made to coexist in a transgenic animal (vertebrate, nematode, drosophila, etc.) in which an aberrant protein is expressed, and a candidate substance may be introduced thereto. The condition for coexistence such as temperature, concentration, pH, time, etc., is not particularly limited, as long as the condition is sufficient for the aberrant protein to bind to VCP and for the candidate substance to effectively inhibit the binding. In particular, a method wherein the candidate substance is introduced by various means into cells in which an aberrant protein and VCP coexists, is preferably exemplified.

Also, the method for confirming whether the binding of the aberrant protein and VCP is inhibited or not by a candidate substance is not limited. For example, a method wherein the aberrant protein is labeled with a tag such as His or Flag or with radioisotopes such as $^{35}$S, and made to contact with VCP immobilized on a carrier for a certain period of time, after which the presence of the labeled signal on the carrier is confirmed, a method wherein the labeled aberrant protein and VCP is mixed and incubated, after which the solution is passed through a column on which a substance that binds to VCP specifically is immobilized, and the presence of the labeled signal on the column or in the eluate is confirmed may be applied. Furthermore, a method of determining whether the inhibition of binding occurs by a candidate substance, by observing the occurrence of vacuolization in the cytoplasm of cells expressing an aberrant protein (for example, PC12/Q79: Yasuda, S., Inoue, K., Hirabayashi, M., Higashiyama, H., Yamamoto, Y., Fuyuhiro, H., Komure, O., Tanaka, F., Sobue, G., Tsuchiya, K., Hamada, K., Sasaki, H., Takeda, K., Ichijo, H., Kakizuka, A., Genes Cells 4, 743–756 (1999)), by the coexistence of VCP and the candidate substance, a method of determining the usefulness of a candidate substance by observing the presence of vacuolization, localization of the aberrant protein and VCP in cells, or change of fluorescence resonance energy transfer (FRET), in the coexistence of VCP labeled with a fluorescent protein such as GFP, YFP, CFP, etc., cells expressing the aberrant protein, and the candidate substance may also be exemplified.

In the method for screening substances of the present invention, experimental techniques generally known in biochemistry, including GST pull-down assay and yeast 2 hybrid method may be applied. Further, BIACORE by which the degree of binding can be confirmed by measuring surface plasmon resonance is preferable for the screening of large quantities of samples. However, methods for screening substances of the present method are not limited to the above examples, as long as the inhibition of the binding of an aberrant protein with VCP by a candidate substance in the coexistence of the aberrant protein, VCP and the candidate substance can be confirmed.

As described above, in the invention of the present application, the method for screening a substance useful as the effective component for prophylactic or therapeutic drugs for neurodegenerative diseases comprises confirming the inhibition of the binding of an aberrant protein with VCP in the coexistence of the aberrant protein, VCP and a candidate substance. The method exemplified above may be conducted under any conditions employing any cells, reagents, concentrations, temperatures, pHs, etc.

In the method for screening substances of the present invention, a candidate substance that is to be screened may be a naturally occurring material such as proteins, amino acids, etc., as well as artificially synthesized polypeptides and a variety of known and novel substances such as polymers and lower molecular weight compounds.

In addition to the above method for screening substances, the present invention provides a kit for screening substances useful as the effective component of prophylactic and therapeutic drugs in neurodegenerative diseases. A variety of screening kits may be considered; those comprising a VCP-immobilized carrier and a labeled aberrant protein are exemplified.

In such a kit, a candidate substance that is expected to inhibit the binding of VCP and the aberrant protein is mixed with a labeled aberrant protein agent; the mixture is poured onto a VCP-immobilized carrier and allowed to stand for a certain period of time, the carrier is washed with a solvent, etc., and whether the candidate substance acts effectively or not maybe the presence of labeled signals on the carrier is observed to confirm confirmed by observing the presence of labeled signals on the carrier. Generation of the labeled signal on the carrier indicates that the aberrant protein binds to VCP immobilized on a carrier, confirming that the screened candidate substance is not appropriate as a prophylactic or therapeutic drug in neurodegenerative diseases. To the contrary, no generation of the labeled signal by the carrier indicates that the binding of VCP with the aberrant protein is inhibited, confirming that the candidate substance is appropriate as a prophylactic or therapeutic drug in neurodegenerative diseases.

In such a kit for screening, the VCP-immobilized carrier may be of any material or form on which VCP can be immobilized, including gel, film, sheet, beads, column, and the like. VCP may be immobilized on the carrier by any means, and a variety of forms such as direct chemical bonding, bonding via segments such as a tag, physical inclusion to beads, etc. may be exemplified. The aberrant protein reagent may be a reagent containing a protein with an extended polyglutamine chain such as MJQ79 (causative protein of Machado-Joseph disease), or a protein for which abnormal conformation is confirmed. In addition it may contain solvents, buffers, additives, etc. The labeling of the aberrant protein may be achieved using any form of labels, for example, various tags such as glutathione S-transferase (GST) or fluorescent proteins, or radio-isotopes. In addition to the VCP-immobilized carrier and the labeled aberrant protein agent, the present kit for screening substances may contain solvents, buffers, additives, various instruments or equipment, etc. The actual process by which the binding of VCP and an aberrant protein is confirmed is not limited to the above procedures and may include various experimental procedures such as protein synthesis, expression of fused proteins, purification by centrifugation or HPLC, electrophoresis such as SDS-PAGE, blotting, etc.

The kit for screening a substance useful as an effective component for prophylactic or therapeutic drugs for neurodegenerative diseases of the present invention may be comprised of a labeled VCP agent and an aberrant protein immobilized on a carrier. By using such a kit, a substance effective as a component for prophylactic or therapeutic drugs for neurodegenerative diseases may be screen by the same process as in the above-exemplified kit. In other words, the labeled VCP agent is mixed with a candidate substance that is expected to inhibit the binding of VCP and the aberrant protein; the mixture is poured onto an aberrant protein immobilized on a carrier and kept under appropriate conditions for a certain period of time, after which the solution is washed out; by observing the presence or absence of the signal from the label, the binding of VCP to the aberrant protein on the carrier is confirmed. Hence, whether the candidate substance effectively acts as prophylactic or therapeutic drugs against neurodegenerative diseases as expected may be confirmed.

Detection of the labeled signal on the carrier indicates the binding of VCP with the aberrant protein, demonstrating that the candidate substance does not inhibit the binding and is not effective as a component for prophylactic or therapeutic drugs for neurodegenerative diseases. On the other hand, observation of no labeled signal on the carrier indicates that the candidate substance inhibits the binding of VCP and the aberrant protein, demonstrating that the candidate substance sufficiently works as a component for prophylactic or therapeutic drugs of neurodegenerative diseases.

The form and material of the carrier, and the components other than the labeled VCP in the reagent are not limited for such kit, as well. Further, the actual procedure by which the binding of VCP and the aberrant protein is confirmed is not limited to the above-described means, and various experimental procedures such as synthesis of proteins, expression of fused proteins, purification by centrifugation or HPLC, electrophoresis such as SDS-PAGE, blotting, and the like, may be included. Of course, the kit for screening substances of the present invention may contain instruments, reagents, and solvents necessary for conducting these procedures.

Modes of the present invention is described in further detail with reference to the attached Figures. Of course, the present invention is not limited to the following examples, and various embodiments on details are available.

EXAMPLES

Example 1

Figure 1:
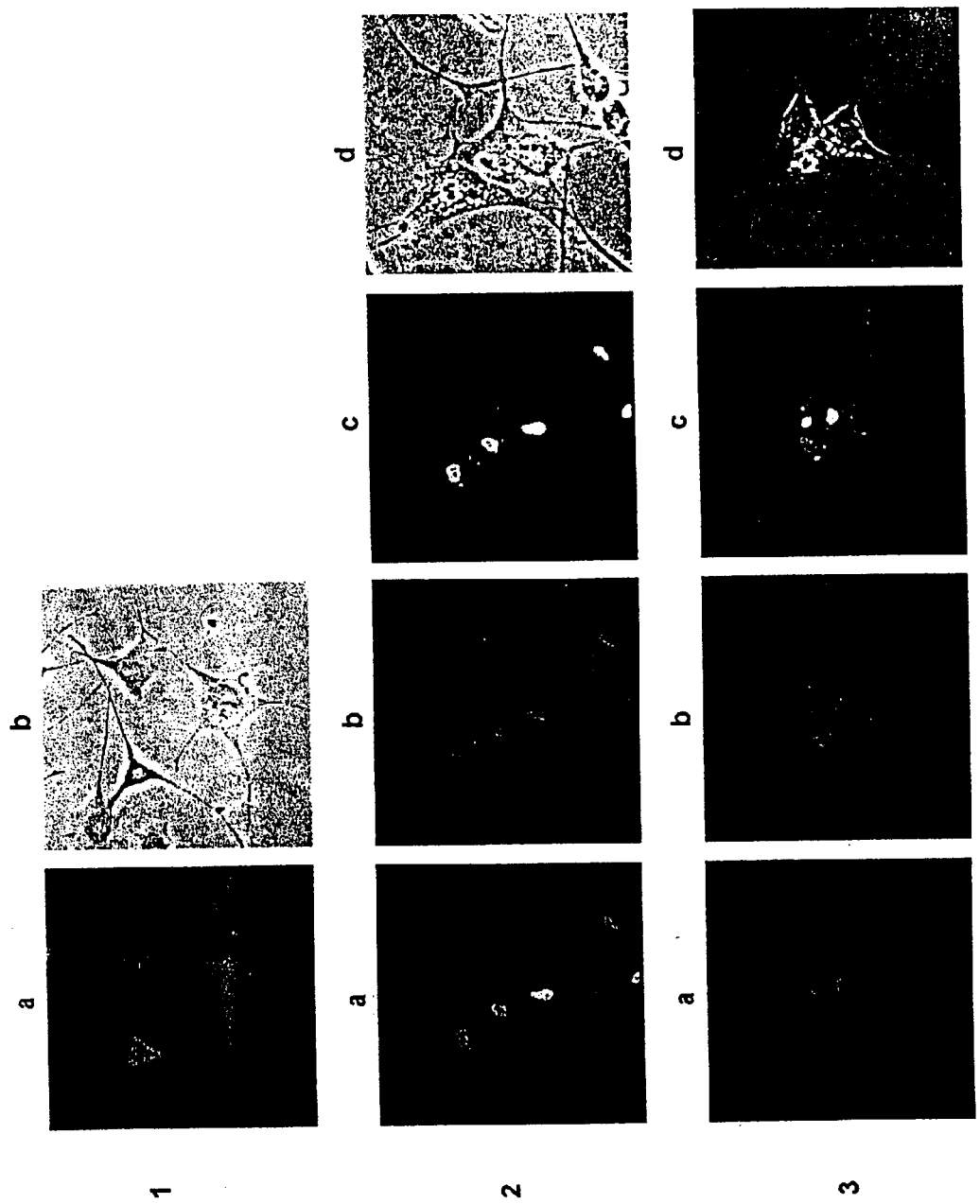
FIG. 1 is a fluorescence micrograph and an optical micrograph showing the localization of VCP protein and the expressed polyglutamine in the PC12 cells (PC12/Q79) which express the Flag tagged-79 repeat polyglutamine (Q79) by removing tetracycline in the Example of the present invention.

Aggregation of Polyglutamine Due to Binding of VCP and a Protein Containing Polyglutamine Chain PC12 cells were fixed, stained using anti-VCP antibody as the first antibody and FITC-labeled anti-rabbit antibody as the 2nd antibody, and observed under a fluorescent microscope to investigate the localization of intrinsic VCP. FIG. 1-1 shows pictures under a fluorescent microscope (a) and an optical microscope (b). Thus, it was confirmed that VCP was expressed throughout the cells.

Next, tetracycline was eliminated from the culture medium of PC12/Q79, and 79-repeat-polyglutamine (Q79) with Flag tag was expressed. After 48 and 96 hours from the elimination of tetracycline, the cells were fixed, and the localization of the intrinsic VCP and polyglutamine were observed. The cells were stained with anti-VCP antibody (FITC-labeled anti-rabbit antibody was used as the second antibody) and anti-Flag antibody (texas red-labeled anti-mouse antibody was used as the second antibody), and the expression of VCP and polyglutamine as well as their localization were observed.

The fluorescent micrograph are shown in FIGS. 1-2a to c (after 48 hours) and FIGS. 1-3a to c (after 96 hours). The optical micrographs of PC12/Q79 cells after expression of polyglutamine are shown in FIG. 1-2d (after 48 hours) and FIG. 1-3d (after 96 hours).

From FIG. 1-2, it was confirmed that polyglutamine forms aggregates in the cytoplasm following induction of expression (FIG. 1-2b), and VCP co-localizes with poly-glutamine (FIG. 1-2c).

From FIG. 1-3, it was confirmed that polyglutamine forms aggregates in the nuclei, as well, with the passage of time (FIG. 1-3b), and that VCP also co-localizes with the polyglutamine in the nuclei (FIG. 1-3c).

Moreover, from observations under an optical microscope, vacuolization in the cytoplasm was confirmed with the expression of polyglutamine (FIG. 1-2d, FIG. 1-3d).

Example 2

Binding of VCP with Aberrant Protein MJDQ79 and Confirmation of Binding Inhibition by Chaperone Proteins (Hsp70, HJD-2)

(1) As an aberrant protein containing an extended polyglutamine chain, the causative protein of Machado-Joseph disease, MJDQ79, which contains 79 glutamine residues, was selected.

MJDQ79 was expressed as a fusion protein of glutathione S-transferase (GST) in *Escherichia coli*.

VCP was expressed in vitro using a lysate of reticulocytes and labeled with $^{35}S$.

GST-MJDQ79 bound on glutathione agarose gel beads and $^{35}S$-VCP were mixed and slowly incubated at 4° C. (2 hours); washing and centrifugation were repeated, and the protein that precipitated with the beads were separated by SDS-PAGE and subjected to autoradiography.

(2) Chaperone proteins (Hsp70, HJD-2) were added to GST-MJDQ79 along with VCP to confirm whether or not the binding of VCP and MJDQ79 is inhibited.

The result of autoradiography is shown in FIG. 2a. The amount of materials added to the reaction medium is represented based on the input amount of the materials, which is expressed as 1. The conditions for lanes 1 to 13 are shown in Table 1.

TABLE 1

| | Input | | | GST | | | GST-MJDQ79 | | | | | | |
|---|---|---|---|---|---|---|---|---|---|---|---|---|---|
| Lane | 1 | 2 | 3 | 4 | 5 | 6 | 7 | 8 | 9 | 10 | 11 | 12 | 13 |
| VCP | 1 | 0 | 0 | 5 | 0 | 0 | 1 | 1 | 1 | 0 | 1 | 1 | 0 |
| Hsp70 | 0 | 1 | 0 | 0 | 5 | 0 | 0 | 1 | 5 | 5 | 0 | 0 | 0 |
| HJD-2 | 0 | 0 | 1 | 0 | 0 | 5 | 0 | 0 | 0 | 0 | 1 | 5 | 5 |

The amount of VCP in lanes 7, 8, 9, 11 and 12 in FIG. 1a is expressed numerically in the graph of FIG. 2b. The vertical axis is represented with the amount of VCP added in the input expressed as 100.

As can be seen from FIG. 2a, expressing the amount of VCP as 1, when the amount of Hsp70 was increased from 0 to 1 and 5, the VCP band became weaker (FIG. 2a; lanes 7, 8 and 9). The VCP band also became weaker as the amount of HJD-2 was increased from 0 to 1 to 5 (FIG. 2a: lanes 7, 11 and 12). The decrease in the concentration of these bands was also confirmed from the graph in FIG. 2b. In other words, it was confirmed that the interaction of GST-MJDQ79 and VCP decreases with the increase in amount of Hsp70 and HJD-2 addition.

From the above results, it was confirmed that the binding of VCP and MJDQ79 is inhibited by Hsp70 and HJD-2. Further, it was suggested that such inhibition was caused by the respective binding of Hsp70 and HJD-2 to GST-MJDQ79 (FIG. 2a: lanes 10 and 13).

(3) The MJDQ79 protein was labeled with $^{35}S$ and synthesized in vitro. Further, VCP was expressed as a fusion protein with GST in *Escherichia coli*.

By the same process described in (1), the binding of GST-VCP and $^{35}S$-MJDQ79 was confirmed.

The result of autoradiography is shown in FIG. 2c. The input amount of materials is expressed as 1, and the amount of materials added to the reaction medium are represented based on the input. Conditions for lanes 1 to 14 are shown in Table 2.

TABLE 2

| | Input | | | GST | | | GST-VCP | | | | | | | |
|---|---|---|---|---|---|---|---|---|---|---|---|---|---|---|
| Lane | 1 | 2 | 3 | 4 | 5 | 6 | 7 | 8 | 9 | 10 | 11 | 12 | 13 | 14 |
| MJDQ79 | 1 | 0 | 0 | 5 | 0 | 0 | 1 | 1 | 1 | 5 | 5 | 5 | 0 | 0 |
| Hsp79 | 0 | 1 | 0 | 0 | 5 | 0 | 0 | 5 | 0 | 0 | 5 | 0 | 5 | 0 |
| HJD-2 | 0 | 0 | 1 | 0 | 0 | 5 | 0 | 0 | 5 | 0 | 0 | 5 | 0 | 5 |

The amount of MJDQ79 in lanes 10, 11 and 12 of FIG. 2c is expressed numerically in FIG. 2d. The vertical axis is represented with the amount of MJDQ79 added in the input expressed as 100.

As can be seen from FIG. 2c, compared to the band of GST-VCP in coexistence with MJDQ79 alone, the band was weaker when Hsp7O was in coexistence (FIG. 2c: lanes 10 and 11). Additionally, the band of MJDQ79, GST-VCP and HJD-2 also became weaker than that of MJDQ79 alone in coexistence with GST-VCP (FIG. 2c: lanes 10 and 12).

Such decrease in the concentration of the band was also confirmed from the graph in FIG. 2d. In other words, it was demonstrated that the interaction of MJDQ79 and GST-VCP decreases in the system wherein Hsp70 and HJD-2 were added.

From the above results, it was confirmed that the binding of VCP and MJDQ79 is inhibited by Hsp70 and by HJD-2.

Further, it was suggested that such inhibition was caused by the respective binding of Hsp70 and HJD-2 to GST-VCP (FIG. 2c: lanes 13 and 14).

Example 3

Relaxation Mechanism of Polyglutamine Induced Neurodegeneration by Chaperone Proteins (Hsp70 and HJS-2)

It has been reported that neurodegeneration caused by polyglutamine can be alleviated by excess expression of a chaperone proteins such as Hsp701 or HJD-2 (Hsp40 family) (Warrick, J. M., Chan, H. Y., Gray-Board, G. L., Chai, Y., Paulson, H. L., Bonini, N. M., Nat. Genet. 23, 425–428 (1999); Kazemi-Esfarijani, P., Benzer, S., Science 287, 1837–1840 (2000); Muchowski, P. J., Schaffar, G., Sittler, A., Wanker, E. E., Hayer-Hartl, M. K., Hartl, F. U., Proc. Natl. Acad. Sci. USA, 97, 7841–7846 (2000)). However, the mechanism by which such proteins inhibit the polyglutamine neurodegeneration has not been known up to now.

From the results of the above Example 2, it was indicated that Hsp70 and HJS-2 independently bind to VCP and the polyglutamine-containing protein and competes with the binding of VCP and the aberrant protein to inhibit the binding in a dose-dependent manner.

Accordingly, a mechanism wherein the chaperone protein inhibits the binding of VCP to polyglutamine, whereby reducing the toxicity of polyglutamine, was elucidated.

From the above results, changing the amount or combination of chaperone proteins may enable stronger inhibition of the binding.

In other words, it was confirmed that the inhibition of the binding of VCP with polyglutamine is an effective indicator in screening drugs that reduce the toxicity of polyglutamine.

Example 4

The Binding of VCP with a Precursor Protein of Amyloid β-Protein

The precursor of amyloid β-protein (APP: in this experiment, the sequence from the β-secretase cleavage site to the C-terminal is indicated), which is known as the causative protein of Alzheimer's disease, was synthesized in vitro and labeled with $^{35}S$. GST-VCP was mixed with $^{35}S$-APP, and the mixture was incubated at 4° C. for 2 hours, separated by SDS-PAGE, and subjected to autoradiograhy.

A protein containing an extended poly-glutamine (MJDQ79) was used as a positive control, and a protein containing no domain of glutamine region (MJDΔQ) was used as a negative control.

The results of autoradiography are shown in FIG. 3. As shown in the figure, the lanes indicate, from left to right, the Input (synthesized protein), precipitate with GST alone, and precipitate with GST-VCP.

As in Examples 1 and 2, it was confirmed that the MJD protein is capable of binding with VCP in the presence of polyglutamine, but not in the absence of polyglutamine.

Similarly, it was confirmed that the aberrant protein AAP binds to VCP.

Therefore, it was suggested that the screening of substances that inhibit the binding of the aberrant protein (APP) and VCP is effective even for the identification of substance effective as prophylactic or therapeutic drugs for Alzheimer's disease, a neurodegenerative diseases caused by an aberrant protein other than those containing an extended polyglutamine chain.

Example 5

Binding of VCP and Lewy Bodies in Dementia with Lewy Bodies (DLB)

Lewy bodies collected from a patient suffering from DLB, dementia where in addition to lesion in the brainstem as in Parkinson's disease, the appearance of Lewy bodies in the cerebral cortex occurr, were stained with an anti-VCP antibody As shown in FIG. 4, the Lewy bodies were stained with anti-VCP antibody.

From this result, the presence of binding between VCP with the Lewy bodies, which is a phenotype of DLB, was confirmed. Therefore, it is suggested that identification of substances useful as the effective component of prophylactic or therapeutic drugs for DLB would be possible by screening substances that inhibit the binding.

Example 6

Binding of VCP with a Ubiquitin-Positive Nuclear Inclusion Body of Spinal Cerebral Degeneration The ubiquitin-positive nuclear inclusion body in a patient with spinal cerebral degeneration that occurred in infancy and rapidly progressed was stained with anti-ubiquitin antibody and anti-VCP antibody, respectively.

From FIG. 5, it was confirmed that the ubiquitin-positive nuclear inclusion body is stained with anti-ubiquitin antibody (FIG. 5a) as well as with anti-VCP antibody (FIG. 5b).

From this result, the binding of VCP and the ubiquitin-positive nuclear inclusion body of spinal cerebral degeneration was confirmed. Therefore, it is suggested that by screening substances that inhibit such binding, identification of substances that are useful as the effective component of prophylactic or therapeutic drugs against spinal cerebral degeneration would be possible.

Industrial Applicability

As described above in detail, the present invention provides a method for screening substances useful as the effective component of prophylactic or therapeutic drugs for neurodegenerative diseases. The invention also provides a kit for screening substances effective as components in prophylactic or therapeutic drugs for neurodegenerative diseases. Research, development and commercialization of prophylactic or therapeutic drugs for neurodegenerative diseases can be expected to accelerate, by using the screening method and the screening kit of the present invention.

What is claimed is:

1. A method for screening substances that inhibit binding of an aberrant protein to a valosin-containing protein, comprising the steps of:

isolating and preparing the aberrant protein;

isolating and preparing the valosin-containing protein;

making the aberrant protein and the valosin-containing protein and a candidate substance coexist in a state where interaction may occur; and identifying the substance that shows inhibitory action on the binding of the aberrant protein to the valosin-containing protein, wherein the aberrant protein is selected from the group consisting of polyglutamine-containing proteins, Aβ, α-synuclein, and SOD1.

2. The method for screening a substance of claim 1, wherein the aberrant protein and the valosin-containing protein and the candidate substance are made to coexist by mixing in a solution.

3. The method for screening a substance of claim 1, wherein the aberrant protein and the valosin-containing protein and the candidate substance are made to coexist in a culture cell.

4. The method for screening a substance of claim 1, wherein the aberrant protein and the valosin-containing protein and the candidate substance are made to coexist by administering each component to an animal.

5. The method for screening a substance of claim 1, wherein the inhibitory action is detected by:

labeling either the aberrant protein or the valosin-containing protein;

immobilizing the non-labeled protein on a carrier;

making the aberrant protein and the valosin-containing protein contact in the presence of the candidate substance; and detecting the signal generated by the labeled protein on the immobilized carrier.

6. The method for screening a substance of claim 1, wherein the aberrant protein is a polyglutamine containing protein.

7. The method for screening a substance of claim 6, wherein the polyglutamine containing protein is MJQ79.

* * * * *